US006540390B2

(12) United States Patent
Toth et al.

(10) Patent No.: US 6,540,390 B2
(45) Date of Patent: *Apr. 1, 2003

(54) INTENSITY CONTROLLABLE HAND-HELD SURGICAL LIGHT

(75) Inventors: Cynthia A. Toth, Durham, NC (US); Ronald F. Overaker, Durham, NC (US); Brian C. Dodge, Durham, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/123,150

(22) Filed: Apr. 17, 2002

(65) Prior Publication Data

US 2002/0126501 A1 Sep. 12, 2002

Related U.S. Application Data

(60) Continuation of application No. 09/657,129, filed on Sep. 7, 2000, now Pat. No. 6,436,035, which is a division of application No. 09/286,659, filed on Apr. 6, 1999, now Pat. No. 6,270,491.

(51) Int. Cl.$^7$ ............................................ A61C 3/00
(52) U.S. Cl. ...................................... 362/552; 362/109
(58) Field of Search .................... 362/90, 109, 321, 362/552, 572, 577, 573, 802, 322, 295, 804; 606/10, 249, 11, 12; 600/249

(56) References Cited

U.S. PATENT DOCUMENTS

| 4,241,246 A | 12/1980 | Lugaresi ................. 200/52 R |
| 4,385,344 A | 5/1983 | Gonser ...................... 362/32 |
| 4,517,974 A | 5/1985 | Tanner ................... 128/303.1 |
| 4,785,796 A | 11/1988 | Mattson ..................... 128/9 |
| 5,098,292 A | 3/1992 | Lazarof .................... 433/141 |
| 5,438,177 A | 8/1995 | Fagan ...................... 200/517 |
| 5,580,147 A | 12/1996 | Salerno ..................... 362/32 |
| 5,634,711 A | 6/1997 | Kennedy et al. ............ 362/119 |
| 5,769,523 A | 6/1998 | Feinbloom .................. 362/32 |
| 5,832,159 A | 11/1998 | Davis ....................... 385/53 |
| 6,054,664 A | 4/2000 | Ariga et al. ............... 200/512 |
| 6,079,861 A | 6/2000 | Woodward et al. ......... 362/552 |
| 6,089,740 A | 7/2000 | Forehand et al. .......... 362/573 |
| 6,123,545 A | 9/2000 | Eggler et al. .............. 433/29 |
| 6,142,650 A | 11/2000 | Brown et al. .............. 362/259 |
| 6,186,944 B1 | 2/2001 | Tsai ........................ 600/200 |
| 6,436,035 B1 * | 8/2002 | Toth et al. ................. 632/572 |

* cited by examiner

Primary Examiner—Stephen Husar
Assistant Examiner—Bao Truong
(74) Attorney, Agent, or Firm—Nixon & Vanderhye P.C.

(57) ABSTRACT

A hand-held surgical light assembly is provided with a light source, and a handpiece which is adapted to be grasped and manipulated by a user. The handpiece has a light guide with a proximal end optically connected to the light source, and a distal end which projects outwardly from said handpiece so as to direct light guided thereby onto a field of view determined by manipulation of the handpiece by the user. The handpiece includes a switch assembly which is operatively coupled to the light source to allow user selection between at least two different light intensities (e.g., essentially on/off) discharged by said light guide onto the field of view. In preferred forms, the switch assembly includes an electrically conductive inner base member and an electrically conductive outer tubular elastomeric member concentrically positioned in surrounding, but spaced relationship, with the inner base member. When contact between the inner base member and the outer elastomeric member is made, switch circuitry changes the visible light intensity of the visible light generated by the light source, e.g., by either directly modulating the current to the lamp itself, or by providing an electrically operable shutter assembly which masks the light generated by the light source. The former embodiment is especially well suited for surgical lights which are self-contained (i.e., have the light sources contained in the handpiece), while the latter is especially well suited for surgical lights which have remotely positioned light sources.

34 Claims, 9 Drawing Sheets

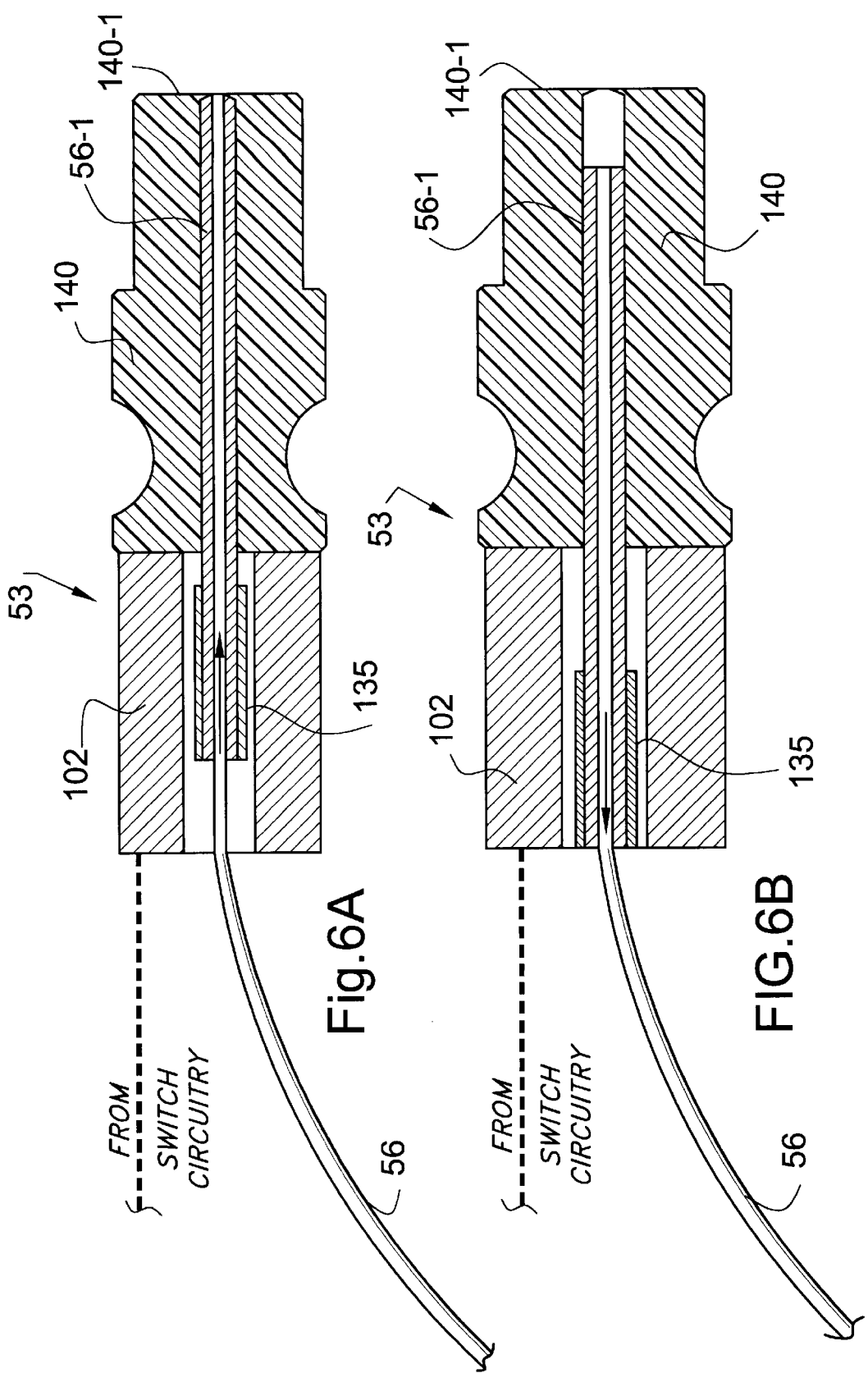

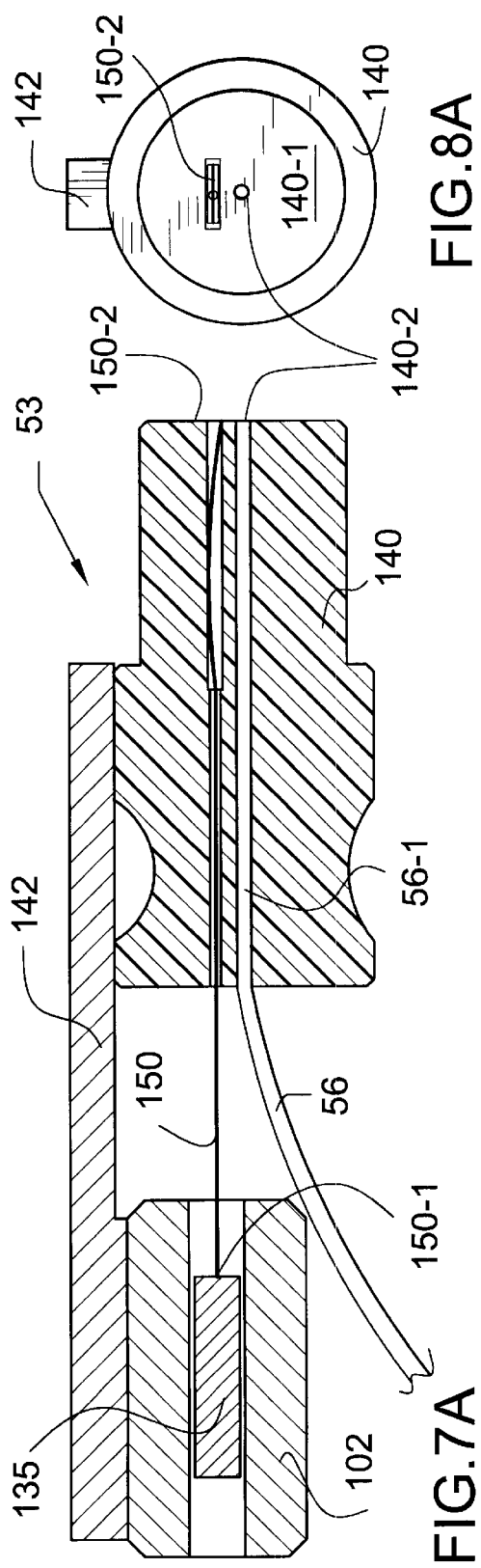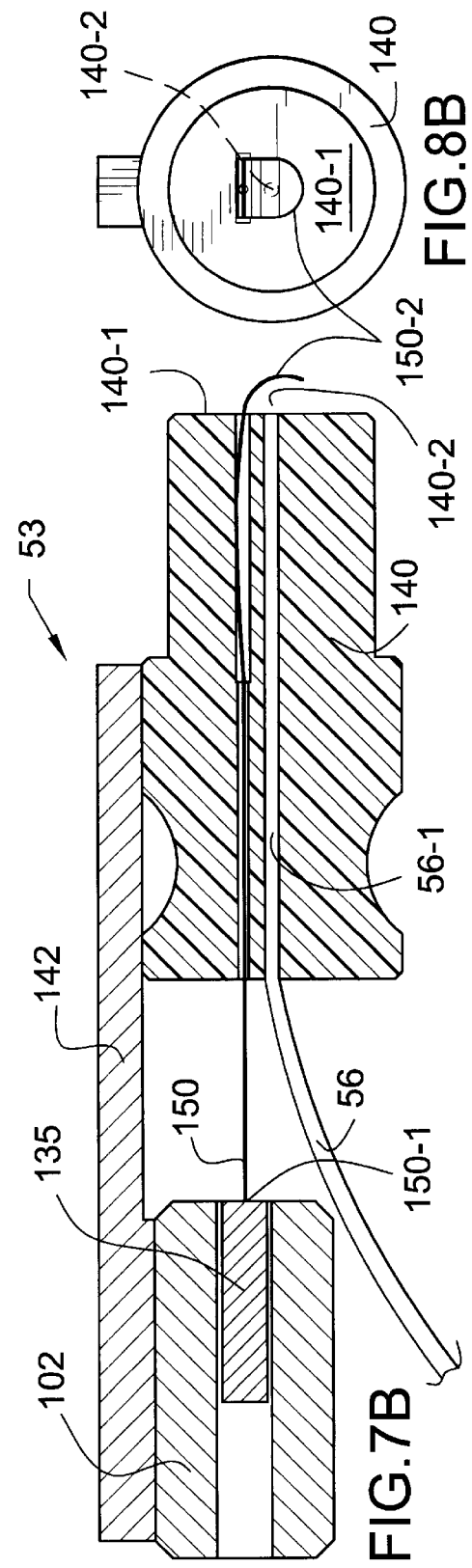

INTENSITY CONTROLLABLE HAND-HELD SURGICAL LIGHT

This is a continuation of application Ser. No. 09/657,129, filed Sep. 7, 2000, now U.S. Pat. No. 6,436,035, which in turn is a divisional application of application Ser. No. 09/286,659 filed On Apr. 6, 1999 (now U.S. Pat. No. 6,270,491 B1), the entire content of each being hereby incorporated expressly by reference in this application,

FIELD OF THE INVENTION

The present invention relates generally to visible light-producing implements used in surgical arenas, especially during ophthalmic surgical procedures. In preferred forms, the present invention is embodied in a hand-held light that permits the surgeon (or other attending surgical personnel) to locally controllably adjust the emitted light intensity.

BACKGROUND AND SUMMARY OF THE INVENTION

Photon energy delivered to the retina from intraocular fiberoptic instruments during ophthalmic surgical procedures can damage the retina. Retinal damage occasioned by such photon energy is known colloquially in the ophthalmic surgical art as "light toxicity". As a result, concerns have arisen over the amount of photon energy being delivered to the retina during a normal surgical procedure. For example, wavelengths from 400 nm to 700 nm are considered to be the safest for purposes of ophthalmic surgery.

However, even at these wavelengths, retinal damage can occur if retinal exposure to the photon energy is prolonged. In this regard, exposure of the retina to light emanating from intraocular fiberoptics during retinal surgery has, in some cases, resulted in pathologic retinal lesions, some of which have been associated with vision loss. Fiberoptic illumination of the retina, however, remains an essential component of vitreoretinal surgery in order for the surgeon to visualize the tissues undergoing the surgical procedure.

Although the use of visible light within the eye during ophthalmic surgery cannot be eliminated, the desire has been to reduce the amount of photon energy being delivered to the retina during a procedure. For example, light sources that have little of the most harmful wavelengths—i.e., light sources which emit little or no photon energy at wavelengths other than between 400–700 nm—have been employed. However, as noted previously, retinal damage can ensue if exposure is prolonged even at these relatively "safe" wavelengths. Furthermore, filters have also been placed in the light path of the light source so as to block the less safe wavelengths. Also, attempts have been made to diffuse the light over larger areas.

Conventional fiberoptic illuminators used to transmit photon energy during ophthalmic surgery are typically formed of polymethylmethacrylate (PMMA) having a nominal numeral aperture (NA) of about 0.66. Most of the energy from these conventional PMMA fiberoptic illuminators is within a 60° cone of light. Some special use fiberoptic lights use glass fibers that have similar optical properties. These conventional illuminators receive their light energy from a standard light source with matching optics allowing for good collection of the energy into the fiber. The fiberoptics are usually of an extended length (e.g., typically about six (6) feet in length) to allow the light emitting end to be used within the surgical field while the light source is maintained in a remote location. The fiberoptics are thus typically draped from the source to the operating field. Since several fiberoptic lights can be in use simultaneously during an operation, the fiberoptics tend to form a tangle of cables running onto the operating field, thereby providing practical complications.

Furthermore, during surgery, there exist the competing demands of providing the surgeon with adequate light to illuminate the surgical field, while at the same time permit relatively instantaneous adjustment of the illumination when desired to thereby reduce the photon energy delivered during periods when full illumination is not needed for the procedure. The surgeon can request that an assistant adjust the intensity of the light at the remotely positioned light source during portions of the surgery when this is feasible or can direct the light away from the most critical portion of the retina (the macula) during pauses in surgery. However, the former technique is problematic since surgical assistants are usually tasked with other responsibilities and thus may not be available to instantaneously adjust the light intensity at the surgeon's request. And, the latter technique may not always be available to the surgeon since the surgeon's hands may be occupied physically with another aspect of the surgical procedure which prevents redirection of the light.

Thus, as can be appreciated from the discussion above, improvements to surgical lights have been needed. It is towards providing such improvements that the present invention is directed.

Broadly, the present invention is embodied in hand-held surgical light assemblies having a light source, and a hand-piece which is adapted to be grasped and manipulated by a user. The handpiece has a light guide with a proximal end optically connected to the light source, and a distal end which projects outwardly from said handpiece so as to direct light guided thereby onto a field of view determined by manipulation of the handpiece by the user. The handpiece includes a switch assembly which is operatively coupled to the light source to allow user selection between at least two different light intensities (e.g., essentially on/off) discharged by said light guide onto the field of view.

In preferred forms, the switch assembly includes an electrically conductive inner core and an electrically conductive outer tubular elastomeric member concentrically positioned in surrounding, but spaced relationship, with the inner base. When contact between the inner base and the outer elastomeric member is made, switch circuitry changes the visible light intensity of the visible light generated by the light source, e.g., by either directly modulating the current to the lamp itself, or by providing an electrically operable shutter assembly which masks the light generated by the light source. The former embodiment is especially well suited for surgical lights which are self-contained (i.e., have the light sources contained in the handpiece), while the latter is especially well suited for surgical lights which have remotely positioned light sources.

These, and other, aspects and advantages will become more clear after careful consideration is given to the following detailed description of the preferred exemplary embodiments thereof.

BRIEF DESCRIPTION OF THE ACCOMPANYING DRAWINGS

Reference will hereinafter be made to the following drawings in which like reference numerals throughout the various FIGURES denote like structural elements, and wherein, FIG. 1 is a perspective view of a particularly preferred embodiment of a self-contained hand-held surgical light in accordance with the present invention;

Figure 3:
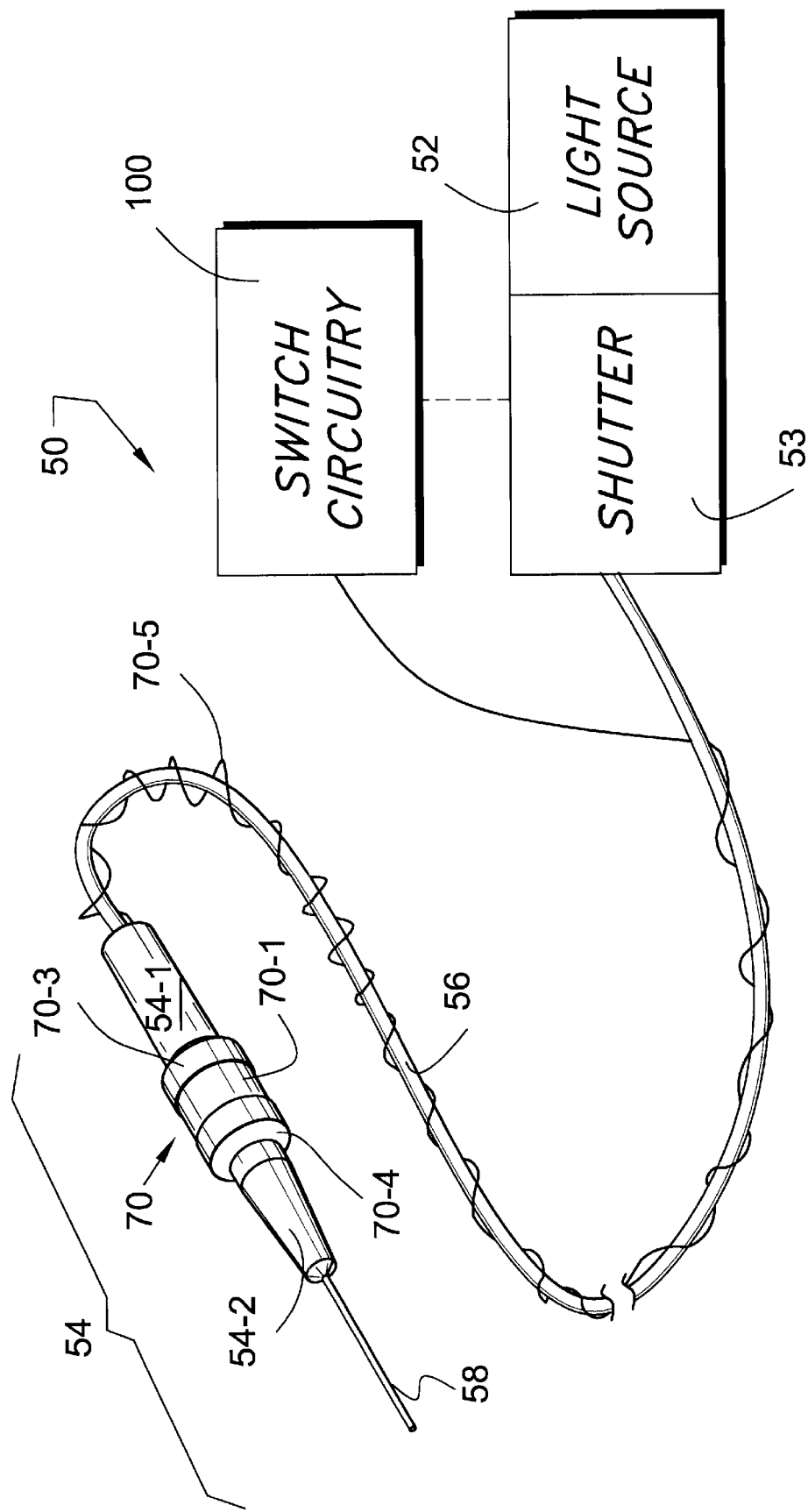
FIG. 3 is a perspective view of another embodiment of a hand-held surgical light assembly in accordance with the present invention which is especially well suited for use in combination with a remotely positioned light source.
Figure 9:
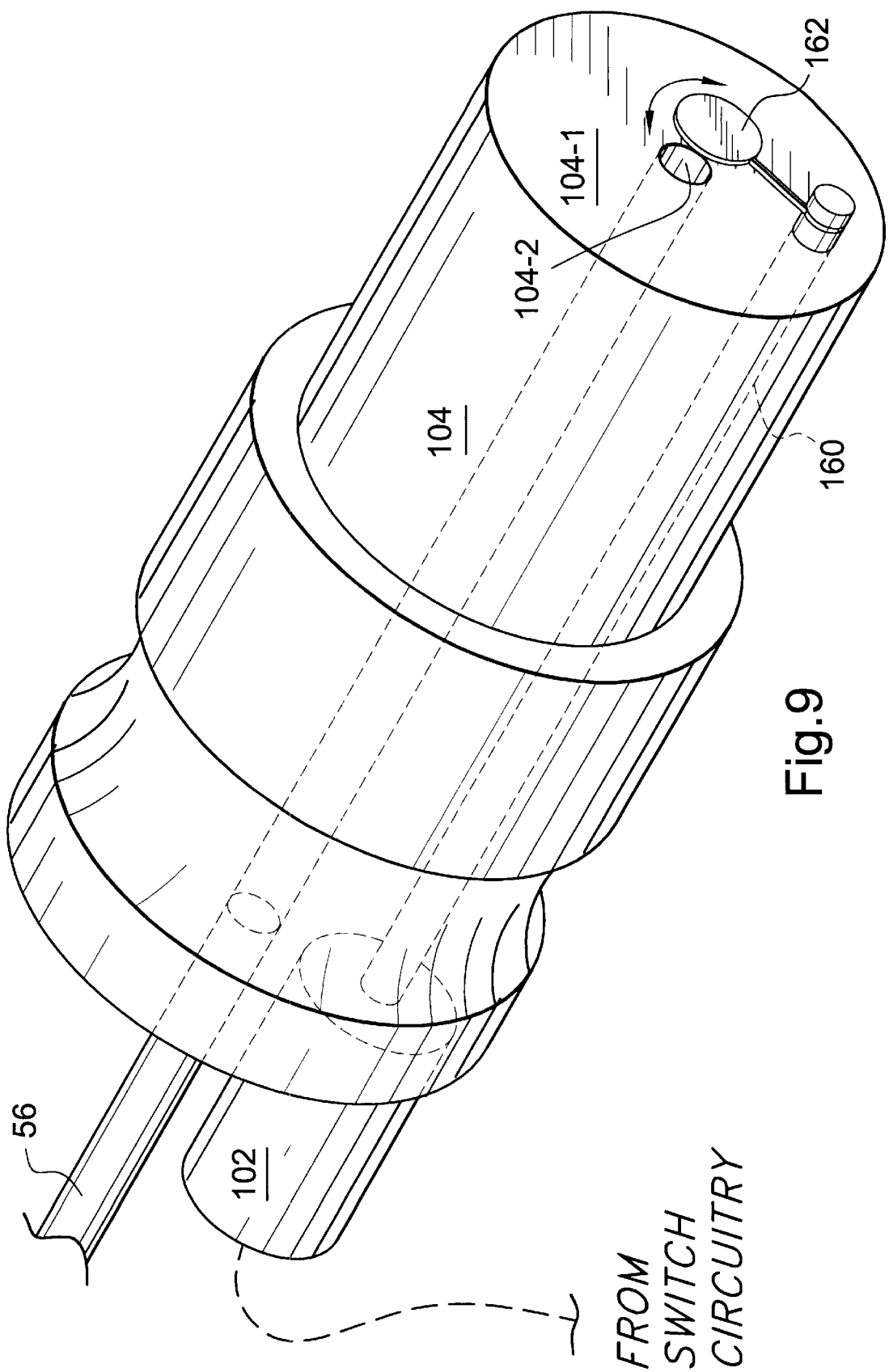
Figure 10:
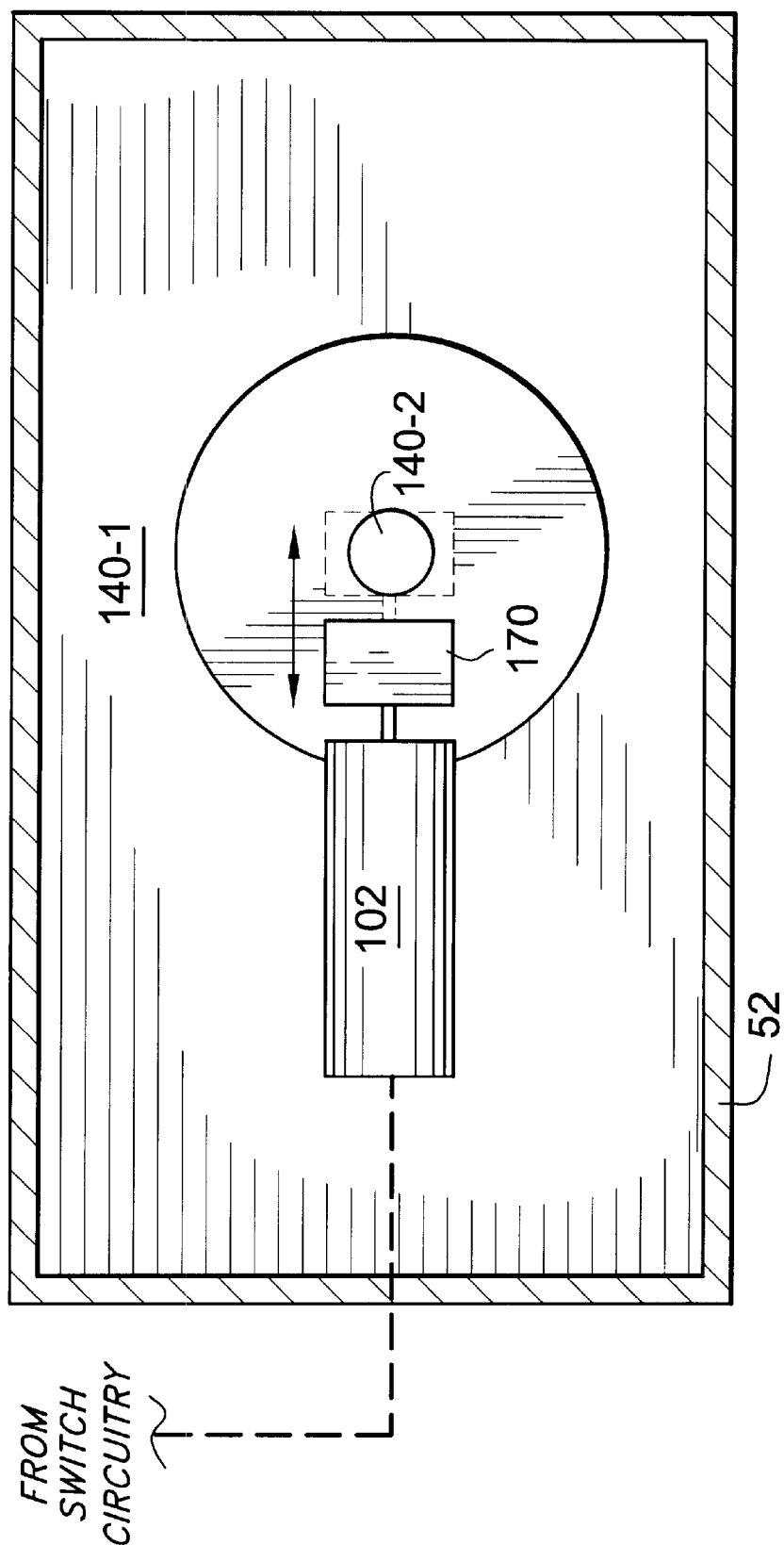

FIGS. 6A and 6B respectively depict different operational states of a shutter assembly that may be employed in operative association with the remotely positioned light source used in surgical light assembly depicted in FIG. 3;

FIGS. 7A and 7B respectively depict different operational states of another shutter assembly that may be employed in operative association with the remotely positioned light source used in surgical light assembly depicted in FIG. 3;

FIGS. 8A and 8B are end elevational views of the shutter states depicted in FIGS. 7A and 7B, respectively, as taken along lines 8A—8A and 8B—8B therein;

FIG. 9 is a rear perspective view of an embodiment of a rotary shutter assembly that may be employed in the surgical light assembly depicted in FIG. 3; and FIG. 10 is a rear cross-sectional elevational schematic view of an embodiment of a rectilinearly moveable shutter assembly that may be employed in the surgical light assembly depicted in FIG. 3.

DETAILED DESCRIPTION OF THE INVENTION

Figure 1:
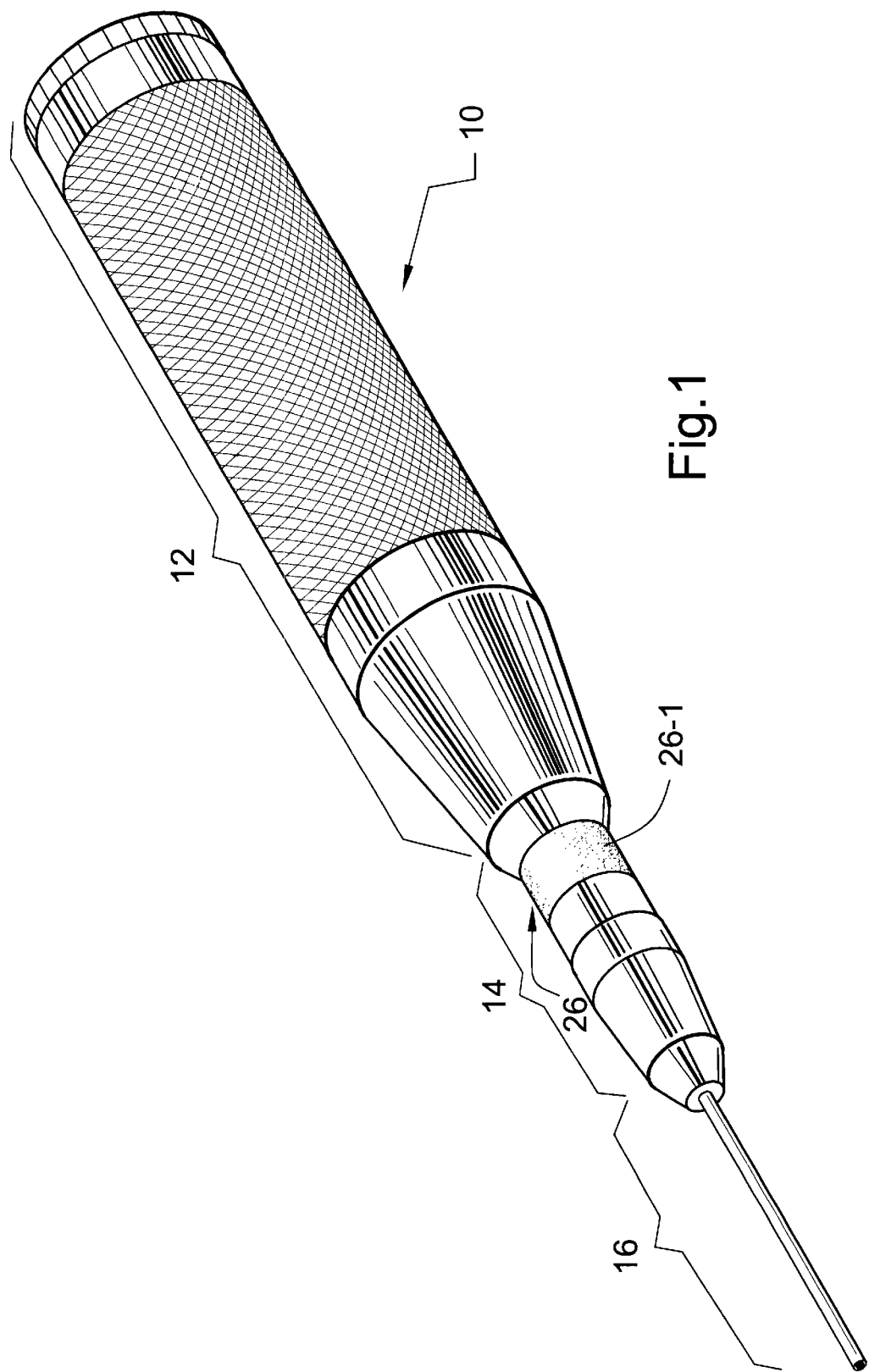
Figure 2:
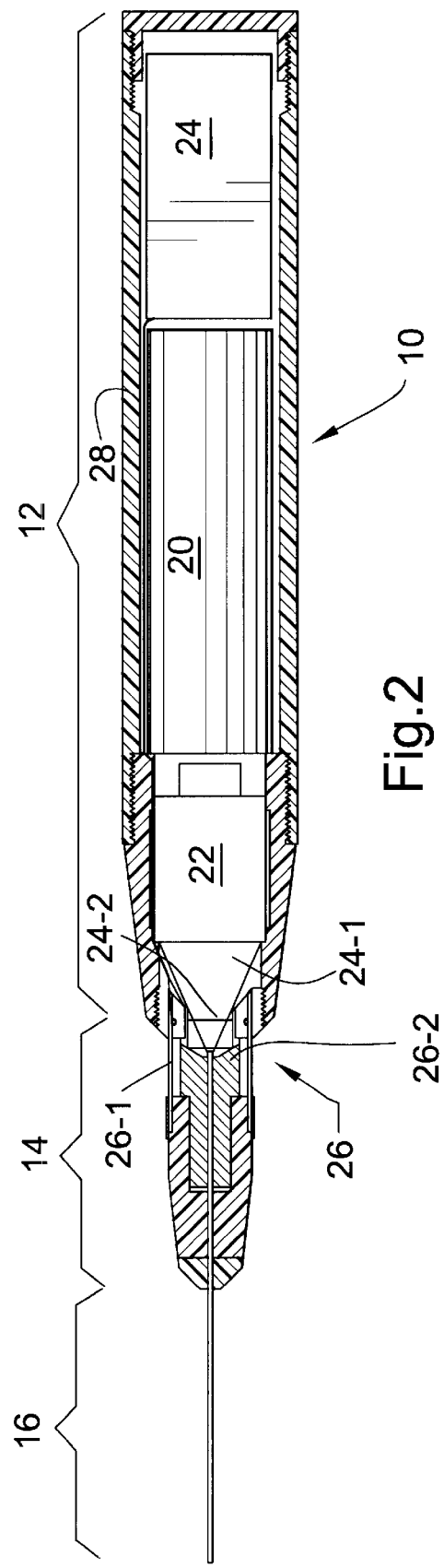
FIG. 2 is a longitudinal cross-sectional view, partly schematic, of the hand-held surgical light depicted in FIG. 1.

One preferred embodiment of a hand-held surgical light 10 in accordance with the present invention is depicted in accompanying FIGS. 1 and 2. The surgical light 10 shown in FIGS. 1 and 2 generally includes a proximal handle section 12 which is sized and configured to be held comfortably in a surgeon's hand, a distal end section 14, and a light guide section 16 protruding distally from the end section 14.

The embodiment of the surgical light 10 shown in accompanying FIGS. 1 and 2 is self-contained. That is, the surgical light 10 includes all operational components such as power source 20 (e.g., preferably in the form of a conventional rechargeable battery), a light source 22 (e.g., a conventional incandescent microbulb), and the electronic switch circuitry 24 are contained within the handle section 12, while a mechanical membrane switch 26 is positioned operatively in the distal end section 14.

The light source 22 includes an ellipsoid mirror (not shown) which focuses the light onto the distally positioned conically shaped mirror 24-1. The light then passes through a wave-length filter 24-2 where potentially harmful wavelengths are filtered therefrom (e.g., so that only photon energy having a wavelength between 400–700 nm passes through the filter 24-2). The filtered light is then directed into the proximal end of the light guide section 16 which is held securely within the distal tip section 14 of the surgical light 10.

The filtered light then propagates along the light guide section 16 and is discharged from its distal tip onto the surgical field as directed manually by the surgeon holding the light 10. Most preferably, the light guide section includes a 19 gauge stainless steel (type 304) tubing in which a light conducting fiber is positionally fixed (e.g., by suitable bonding adhesive). The light conducting fiber is most preferably 0.75 mm diameter and has a numerical aperture of about 0.6.

An electrical switch on the handle assembly will, when manually activated, cause the intensity of the light emitted by the light source 22 to change. The preferred switch according to this invention is a mechanical membrane switch 26 which is comprised generally of an outer electrically conductive tubular elastomeric membrane sleeve 26-1 and an inner electrically conductive generally cylindrical metal member 26-2. The membrane sleeve 26-1 is most advantageously is about 0.040 inch thick and has a hardness of about 55 Durometer and a resistance value of about 10 K ohms per square. One preferred electrically conductive elastomeric sleeve that may be employed is Product No. F00120880000 commercially available from Patter Products Inc. of Beaverton, Mich. The electrically conductive base member 26-2 is most preferably aluminum, for example, 6061 aluminum alloy.

As shown, the outer membrane sleeve 26-1 is separated from the inner conductive base member 26-2 by an annular space. In use, therefore, the surgeon will depress the membrane sleeve 26-1 until it contacts physically the base member 26-2 thereby electrically closing the switch 26. The switch circuitry 24 (to be explained in greater detail below with regard to FIG. 5) is electrically connected to the switch via internal wiring 28 and will therefore sense this switch closure. Generally, the switch circuitry will change the intensity of the light emitted by the light source 22 in a step-wise manner in response to switch closure. In this way, the surgeon can manually and selectively control the intensity of the light emitted from the distal end of the light guide section 16.

Figure 4:
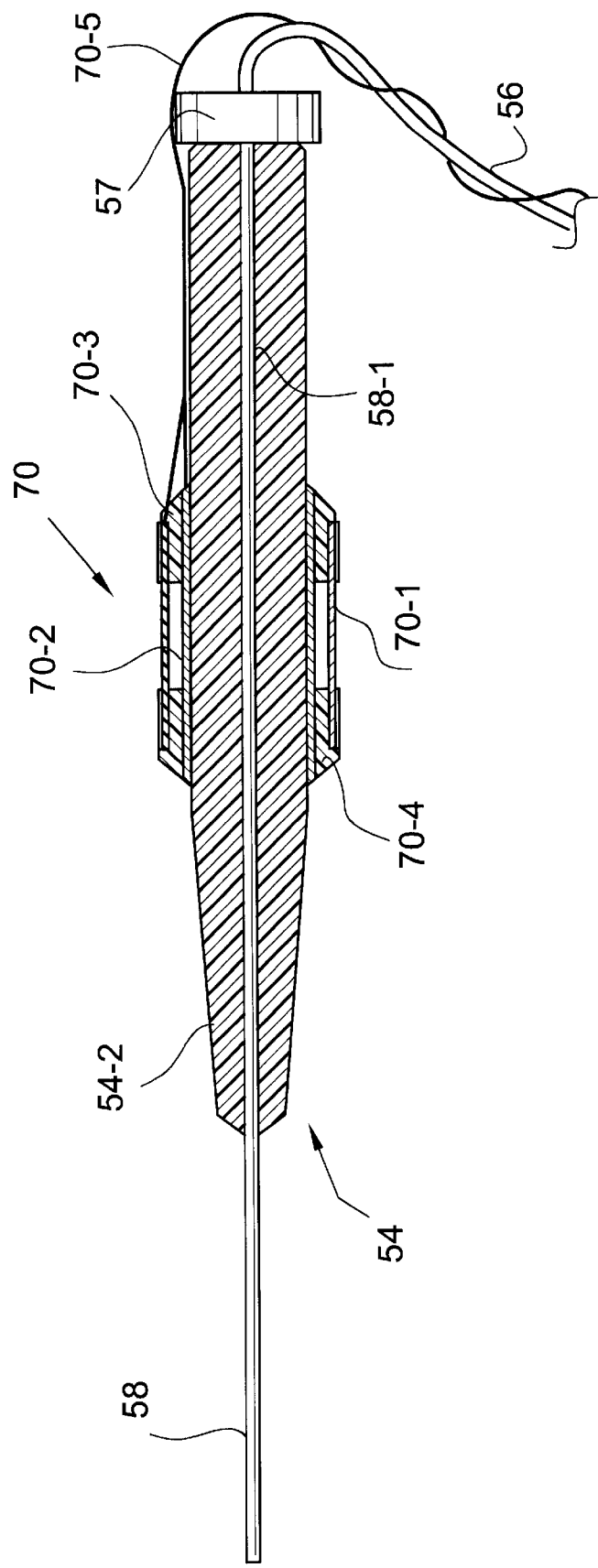
FIG. 4 is an enlarged longitudinal cross-sectional elevation view of the handpiece of the embodiment depicted in FIG. 3.

Accompanying FIGS. 3–4 show another embodiments of a hand-held surgical light 50 in accordance with the present invention. One principal difference between the surgical light 50 depicted in FIGS. 3–4, and the surgical light 10 depicted in FIGS. 1–2 is that the former is not self-contained. Instead, the surgical light 50 includes a remotely located light source 52 which is optically coupled through a shutter assembly 53 to a light probe handpiece 54 via conventional primary optical light guide 56.

The handpiece 54 includes a proximal cylindrical handle section 54-1 sized and configured to allow a surgeon to manually manipulate it during surgical operations and a tapered distal end section 54-2. A light guide section 58 similar to the light guide section 16 discussed previously protrudes outwardly from the distal end section 54-2 of the handpiece 54. The light guide section 58 is optically coupled to the light guide 56 by means of a proximal, and unitary, section 58-1. The handpiece may be coupled/uncoupled from the primary light guide 56 by an optical coupler 57.

According to the present invention, the handpiece 54 carries an electrical switch which, according to the present invention, is most preferably a membrane switch assembly 70. As shown in FIGS. 3 and 4, the membrane switch assembly 70 is sized so as to be sleeved over the handle section 54-1 and be in friction-fit engagement therewith. As is perhaps better seen in FIG. 4, the membrane switch 70 includes an outer conductive tubular elastomeric membrane sleeve 70-1 which concentrically surrounds an inner cylindrical electrically conductive metal base member 70-2. In its normal (non-active) condition, therefore, an annular space is defined between the membrane sleeve 70-1 and the base member 70-2. The membrane sleeve 70-1 and base member 70-2 are electrically isolated from one another while in a normal condition by proximal and distal mounting rings 70-3 and 70-4, respectively. which are separated from one another along the axial direction of the handpiece 50. Most preferably, the electrically conductive elastomeric membrane sleeve 70-1 has the same dimensions and properties as that described above with reference to membrane sleeve 26-1 associated operatively with the surgical light 10. The membrane switch 70 is electrically connected to the switch circuitry 100 via electrical wiring 70-5 traced along the optical light guide 56. Particularly, the switch circuitry 100 may be electrically coupled to a solenoid coil 102 (not shown in FIG. 3, but see FIG. 5) associated operatively with the shutter assembly 53.

Figure 5:
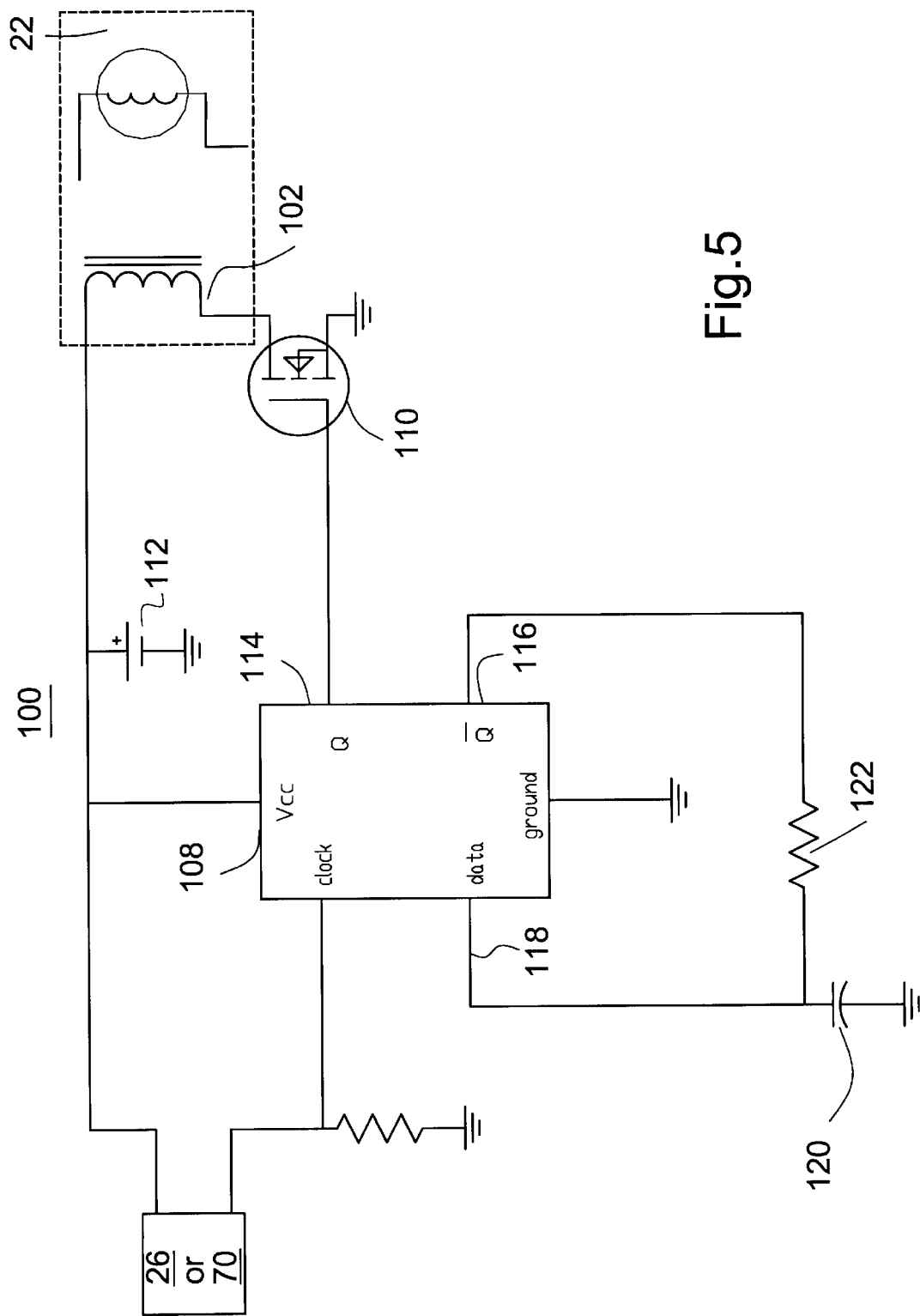
FIG. 5 is a schematic depiction of a control circuit that may be employed in connection with the switches associated with hand-held surgical light embodiments in accordance with the present invention.

Accompanying FIG. 5 depicts an exemplary switching circuit that may be employed as the switch circuit 100 depicted in FIG. 3 or the switch circuit 24 depicted in FIG. 2. Thus, the switch circuit 100 or 24 may operate alternatively a solenoid coil 102 (i.e., if employed in the hand-held surgical light 50) or a light assembly 22 (i.e., if employed in the hand-held surgical light 10), respectively. In this regard, as discussed previously, the mechanical membrane switch 26 (associated with the surgical light 10) or 70 (associated with the surgical light 50) may be activated by the surgeon to effect a change in light intensity in a step-wise manner (most preferably to toggle between on/off states). The membrane switch 26 or 70 is electrically coupled to a flip-flop semiconductor device 108 that controls whether current flows through the switching solenoid coil 102 or light 22 by activating a transistor 110.

The membrane switch applies a reference voltage 112 to the clock input of the flip-flop 108. When the clock signal is high, i.e., reference voltage supplied by the membrane switch, the flip-flop is enabled. Enabling the flip-flop does not by itself cause the outputs 114, 116 to change. The state of the outputs (Q, Q-bar) depends on the data input 118 at the moment the flip-flop 108 is enabled. If the data input is high, then the output (Q) 114 will be switched high when the flip-flop is enabled by the membrane switch. As the output (Q) goes high, then transistor 110 is turned on and current flows through the solenoid coil 102 or light 22.

When the data input 118 is high at the moment the flip-flop 108 is enabled, the inverted output (Q-bar) 116 is switched low. The low state of the Q-bar output will cause the data input 118 to fall to a low state due to the operation of the resistor 122 and capacitor circuit 120 (R/C) connected between the Q-bar output and data input. As long as the data input remains high and capacitor 120 has not discharged, subsequent transitions of the enable signal such as those caused by bounce or uncertain pressure on the membrane switch will cause the Q output 114 to remain high, and transistor 110 will continue to conduct current through the solenoid coil 102 or light 22. After a period of time sufficient for capacitor 110 to discharge through resistor 122 to the Q-bar output 116 and allow the data input 118 to go low, a subsequent closure of the membrane switch will switch the Q output 114 low (and the Q-bar output high). This will turn off transistor 110, which will therefore turn off solenoid coil 102 or light 22. The action of resistor 122 and capacitor 120 will delay the change of data input 118 to the level of Q-bar output 116 as in the previous case, thereby again providing immunity to inadvertent enable signals caused by bounce or uncertain pressure on the membrane switch. This allows the surgeon to turn the light on or off by a momentary activation of the switch, and not have to maintain continuous pressure on the switch. Combining a multiplicity of circuits similar to this, in ways which are completely understood by those skilled in this art, allows for multiple levels of illumination to be selected by the surgeon.

The solenoid coil 102 can be associated operatively with a variety of mechanical shutter systems 53, some embodiments of which will be described below, in combination with the mechanical membrane switch 70. Thus, for example, the shutter assembly 53 may include a shuttle member 135 which is fixed to, and moves axially within the solenoid coil 102. On energization (e.g., by closing the membrane switch 70 as discussed above), as shown in FIG. 6A, the solenoid may drive the proximal section 56-1 of the light guide 56 toward the rear face 140-1 of the optical coupling 140 which couples the light guide 56 to the light source 52. In this condition, the full intensity of the light produced by the light source 52 is allowed to enter and be transferred along the light guide 56. When deenergized (e.g., by closing the membrane switch 70 a subsequent time), the shuttle 135 may be driven in an opposite axial direction as shown in FIG. 6B. In response, therefore, the proximal end section 56-1 of the light guide 56 is recessed within the coupling 140 (i.e., is withdrawn from the face 140-1) thereby diminishing the intensity of the light from light source 52 which is allowed to be propagated along the light guide 56.

Another possible shutter assembly 53 is depicted in accompanying FIGS. 7A–7B and 8A–8B. In this embodiment, the shutter assembly 53 includes a shuttle member 135 which is coaxially moveable between a retracted position (as shown in FIGS. 7A and 8A) and an advanced position (as shown in FIGS. 7B and 8B) within the solenoid coil 102 so as to allow maximum and minimum light intensity to be received by the proximal end section 56-1 of the light guide 56. The solenoid coil 102 is fixed to, and axially spaced from the optical coupling 140 by means of a bridge member 142. A flexible shutter band 150 is attached physically at one end 150-1 to the shuttle member 135 and has an opposite end 150-2 which is capable of covering the entranceway 140-2 to the proximal light guide section 56-1 when the light guide is in its extended position (i.e., as shown in FIGS. 7B and 8B). In this regard, the shutter band 150 is formed of a shape-retaining material and is most preferably bent or curved at the end 150-2 so that, when it protrudes rearwardly from the face 140-1 of the coupling 140, it will bend over and cover the entranceway to the light guide section 56-1. Thus, operating the membrane switch 70 will responsively cause the terminal end 150-2 of the shutter band 150 to respectively be in either a covered and uncovered relationship with respect to the light guide section 56-1 thereby minimizing and maximizing the light it receives from the light source 52.

FIG. 9 depicts another shutter assembly 53 that may be employed in the practice of this invention. In this regard, instead of an axially operable shutter mechanism, the solenoid coil 102 is operable in a rotary direction. The solenoid coil 102 is connected to a proximal end of a drive shaft 160 which extends the entire length of the optical coupling member 104. A paddle-type shutter member 162 is fixed to the distal end of the drive shaft 160. As shown in FIG. 9, operation of the membrane switch 70 causes the solenoid to activate which responsively rotates the drive shaft 160 and thereby swings the paddle-type shutter member 162 into and out of covering relationship with the entranceway 104-2 to the light guide 56 formed in the face 104-1 of the optical coupling 104. The intensity of the light emitted by the light section 58 is thereby minimized and maximized, respectively.

Another paddle-type shutter member 170 depicted in the shutter assembly 53 shown the FIG. 10. In this regard, the shutter member 170 is connected operatively to a solenoid coil which radially reciprocally moves the shutter member 170 into and out of covering relationship with the entranceway 140-2 of the light guide 56 formed in the face 140-1 of the optical coupling member 140. Again, therefore, according to the shutter embodiment depicted in FIG. 10, activation of the switch 70 will responsively cause the shutter member 170 to cover and uncover the light guide entranceway 140-2 thereby minimizing and maximizing the intensity of light discharged from the light guide section 58.

Other equivalent forms and/or embodiments of the present invention, for example, other forms and/or embodiments of the switch assemblies, shutter assembly, and the like, may be envisioned by those skilled in this art. Therefore, while the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A hand-held surgical light assembly comprising:
   a light source; and
   a handpiece adapted to be grasped and manipulated by a user; wherein
   said handpiece has a light guide with a proximal end optically connected to the light source, and a distal end which projects outwardly from said handpiece and directs light guided thereby onto a field of view determined by manipulation of the handpiece by the user; and wherein
   said handpiece includes a switch assembly which is operatively coupled to the light source to allow user selection between a non-illuminated off condition and at least two different illuminated on conditions having two different respective light intensities which are discharged by said light guide onto the field of view.

2. The hand-held light assembly of claim 1, wherein said light source is contained within said handpiece.

3. The hand-held light assembly of claim 2, wherein said handpiece includes a source of electrical power electrically connected to said switch assembly and said light source.

4. The hand-held light assembly of claim 1 or 3, wherein said switch assembly includes an electrically conductive, elastomeric membrane switch.

5. The hand-held light assembly of claim 3, wherein said switch assembly includes an inner electrically conductive base member, and a tubular electrically conductive elastomeric member concentrically surrounding said base member in spaced relationship thereto.

6. The hand-held light assembly of claim 1, wherein said switch assembly includes an inner electrically conductive base member, and a tubular electrically conductive elastomeric member concentrically surrounding said base member in spaced relationship thereto.

7. The hand-held light assembly of claim 6, wherein said light source is remotely positioned relative to said handpiece, and wherein said light source includes an electrically-operable shutter assembly connected operatively to said switch assembly to effect said at least two different light intensities.

8. The hand-held light assembly of claim 7, wherein said base member is cylindrical and is sleeved over said handpiece.

9. The hand-held light assembly of claim 8, wherein said switch assembly includes proximal and distal electrically non-conductive mounting rings which are fixed to and concentrically separate said tubular electrically conductive elastomeric member and said electrically conductive base member.

10. The hand-held light assembly of claim 7, 8 or 9, wherein said shutter assembly includes a solenoid which is actuated in response to actuation of said switch assembly.

11. The hand-held light assembly of claim 10, wherein said solenoid includes a shuttle member connected to a proximal end of said light guide, said shuttle member being moveable to responsively cause said proximal end of said light guide to be moved towards and away from said light source to thereby effect said at least two light intensities.

12. The hand-held light assembly of claim 10, wherein said shutter assembly includes a flexible shutter band having one end connected to a shuttle member moveable within said solenoid and an opposite end moveable into and out of covering relationship with said proximal end of said light guide in response to movement of said shuttle member to there effect said at least two light intensities.

13. The hand-held light assembly of claim 10, wherein said shutter assembly includes a shutter paddle connected operatively to said solenoid for movement into and out of covering relationship with said proximal end of said light guide to effect said at least two light intensities.

14. The hand-held light assembly of claim 13, wherein said shutter paddle is moved radially into and out of said covering relationship with respect to said proximal end of said light guide.

15. The hand-held light assembly of claim 13, wherein said shutter paddle is moved rotationally into and out of said covering relationship with respect to said proximal end of said light guide.

16. The hand-held light assembly of claim 15, wherein said shutter assembly includes a drive shaft disposed generally parallel to said proximal end of said light guide, said drive shaft having one end connected to said solenoid, and an opposite end connected to said shutter paddle such that activation of said solenoid rotates said drive shaft which, in turn, rotates said shutter paddle into and out of said covering relationship.

17. The hand-held light assembly of claim 1, wherein said light source is positioned remotely from said handpiece.

18. The hand-held light assembly of claim 17, wherein said assembly includes a optical fiber element which optically connects said light source and said light guide of said handpiece.

19. A hand-held surgical light assembly comprising:
   a light source; and
   a handpiece adapted to be grasped and manipulated by a user; wherein
   said handpiece has a light guide with a proximal end optically connected to the light source, and a distal end which projects outwardly from said handpiece and directs light guided thereby onto a field of view determined by manipulation of the handpiece by the user; and wherein
   said handpiece includes a switch assembly which is operatively coupled to the light source to allow user selection between at least two different illuminated on conditions having two different respective light intensities which are discharged by said light guide onto the field of view.

20. The hand-held light assembly of claim 19, wherein said light source is contained within said handpiece.

21. The hand-held light assembly of claim 20, wherein said handpiece includes a source of electrical power electrically connected to said switch assembly and said light source.

22. The hand-held light assembly of claim 21, wherein said switch assembly includes an electrically conductive, elastomeric membrane switch.

23. The hand-held light assembly of claim 21, wherein said switch assembly includes an inner electrically conductive base member, and a tubular electrically conductive elastomeric member concentrically surrounding said base member in spaced relationship thereto.

24. The hand-held light assembly of claim 19, wherein said switch assembly includes an inner electrically conductive base member, and a tubular electrically conductive elastomeric member concentrically surrounding said base member in spaced relationship thereto.

25. The hand-held light assembly of claim 24, wherein said light source is remotely positioned relative to said handpiece, and wherein said light source includes an electrically-operable shutter assembly connected operatively to said switch assembly to effect said at least two different light intensities.

26. The hand-held light assembly of claim 25, wherein said base member is cylindrical and is sleeved over said hand-piece.

27. The hand-held light assembly of claim 26, wherein said switch assembly includes proximal and distal electrically non-conductive mounting rings which are fixed to and concentrically separate said tubular electrically conductive elastomeric member and said electrically conductive base member.

28. The hand-held light assembly of claim 25, 26 or 27, wherein said shutter assembly includes a solenoid which is actuated in response to actuation of said switch assembly.

29. The hand-held light assembly of claim 28, wherein said solenoid includes a shuttle member connected to a proximal end of said light guide, said shuttle member being moveable to responsively cause said proximal end of said light guide to be moved towards and away from said light source to thereby effect said at least two light intensities.

30. The hand-held light assembly of claim 28, wherein said shutter assembly includes a flexible shutter band having one end connected to a shuttle member moveable within said solenoid and an opposite end moveable into and out of covering relationship with said proximal end of said light guide in response to movement of said shuttle member to there effect said at least two light intensities.

31. The hand-held light assembly of claim 28, wherein said shutter assembly includes a shutter paddle connected operatively to said solenoid for movement into and out of covering relationship with said proximal end of said light guide to effect said at least two light intensities.

32. The hand-held light assembly of claim 31, wherein said shutter paddle is moved radially into and out of said covering relationship with respect to said proximal end of said light guide.

33. The hand-held light assembly of claim 31, wherein said shutter paddle is moved rotationally into and out of said covering relationship with respect to said proximal end of said light guide.

34. The hand-held light assembly of claim 33, wherein said shutter assembly includes a drive shaft disposed generally parallel to said proximal end of said light guide, said drive shaft having one end connected to said solenoid, and an opposite end connected to said shutter paddle such that activation of said solenoid rotates said drive shaft which, in turn, rotates said shutter paddle into and out of said covering relationship.

\* \* \* \* \*